(12) United States Patent
Blackshear

(10) Patent No.: US 6,187,543 B1
(45) Date of Patent: Feb. 13, 2001

(54) METHOD OF SCREENING A COMPOUND FOR ITS ABILITY TO ENHANCE THE ABILITY OF TRISTETRAPROLIN TO INHIBIT TUMOR NECROSIS FACTOR

(75) Inventor: Perry J. Blackshear, Chapel Hill, NC (US)

(73) Assignee: Duke University, Durham, NC (US)

( * ) Notice: Under 35 U.S.C. 154(b), the term of this patent shall be extended for 0 days.

(21) Appl. No.: 09/294,087

(22) Filed: Apr. 19, 1999

Related U.S. Application Data

(63) Continuation of application No. 08/648,773, filed on May 16, 1996, now abandoned.

(51) Int. Cl.$^7$ ................................................. C12Q 1/68
(52) U.S. Cl. ......................... 435/6; 435/91.1; 435/91.2; 549/354; 564/427
(58) Field of Search ............................. 435/6, 91.1, 91.2; 549/354; 564/427

(56) References Cited

U.S. PATENT DOCUMENTS

| | | |
|---|---|---|
| 5,252,479 | 10/1993 | Srivastava . |
| 5,304,634 | 4/1994 | Schade . |
| 5,393,788 | 2/1995 | Bender et al. . |
| 5,426,181 | 6/1995 | Lee et al. . |
| 5,428,132 | 6/1995 | Hirsch et al. . |
| 5,447,851 | 9/1995 | Beutler et al. . |
| 5,449,687 | 9/1995 | Christensen, IV et al. . |
| 5,486,595 | 1/1996 | Heavner . |
| 5,506,340 | 4/1996 | Heavner . |
| 5,519,000 | 5/1996 | Heavner et al. . |
| 5,547,970 | 8/1996 | Weithmann et al. . |
| 5,567,433 | 10/1996 | Collins . |
| 5,574,173 * | 11/1996 | Ting et al. ............................. 549/354 |
| 5,576,206 | 11/1996 | Schlegel . |
| 5,580,859 | 12/1996 | Felgner et al. . |
| 5,635,380 | 6/1997 | Naftilan et al. . |
| 5,641,680 | 6/1997 | Zhao . |
| 5,641,751 | 6/1997 | Heavner . |
| 5,646,154 | 7/1997 | Irie et al. . |
| 5,648,251 | 7/1997 | Kotani et al. . |
| 5,650,156 | 7/1997 | Grinstaff et al. . |

OTHER PUBLICATIONS

Lai et al, "Promoter Analysis of Zfp–36, Mitgen–inducible Gene Encoding the Zinc Finger Protein Tristetraprolin", The Journal of Biological Chemistry 270(42):25266–25272 (1995).

Taylor et al, "Mitogens Stimulate the Rapid Nuclear to Cytosolic Translocation of Tristetraprolin, a Potential Zinc–Finger Transcription Factor", Molecular Endocrinology 10(2)140–146 (1996).

Taylor et al, "Phosphorylation of Tristetraprolin, a Potential Zinc Finger Transcription Factor, by Mitogen Stimulation in Intact Cells and by Mitogen–activated Protein Kinase in Vitro", The Journal of Biological Chemistry 270(22):13341–13347 (1995).

Lai et al, "Rapid Insulin–stimulated Accumulation of an mRNA Encoding a Proline–rich Protein", The Journal of Biological Chemistry 265(27):16556–16563 (1990).

Taylor et al, "The human TTP protein: sequence, alignment with related proteins, and chromosomal localization of the mouse and human genes", Nucleic Acids Research 19(12):3454 (1991).

Taylor et al, "A Pathogenetic Role for TNFα in the Syndrome of Cachexia, Arthritis, and Autoimmunity Resulting from Tristetraprolin (TTP) Deficiency", Immunity 4:445–454 (1996).*

Orkin et al, "Report and Recommendations of the Panel to Assess the NIH Investment in Research on Gene Therapy", Dec. 7, 1995.*

\* cited by examiner

*Primary Examiner*—Kenneth R. Horlick
*Assistant Examiner*—Janell E. Taylor
(74) *Attorney, Agent, or Firm*—Nixon & Vanderhye P.C.

(57) ABSTRACT

The present invention relates, in general, to tristetraprolin (TTP) and, in particular, to methods of modulating levels of tumor necrosis factor α (TNFα) using TTP or nucleic acid sequences encoding same. The invention further relates to methods of screening for compounds for their ability to inhibit TNFα biosynthesis.

7 Claims, 6 Drawing Sheets

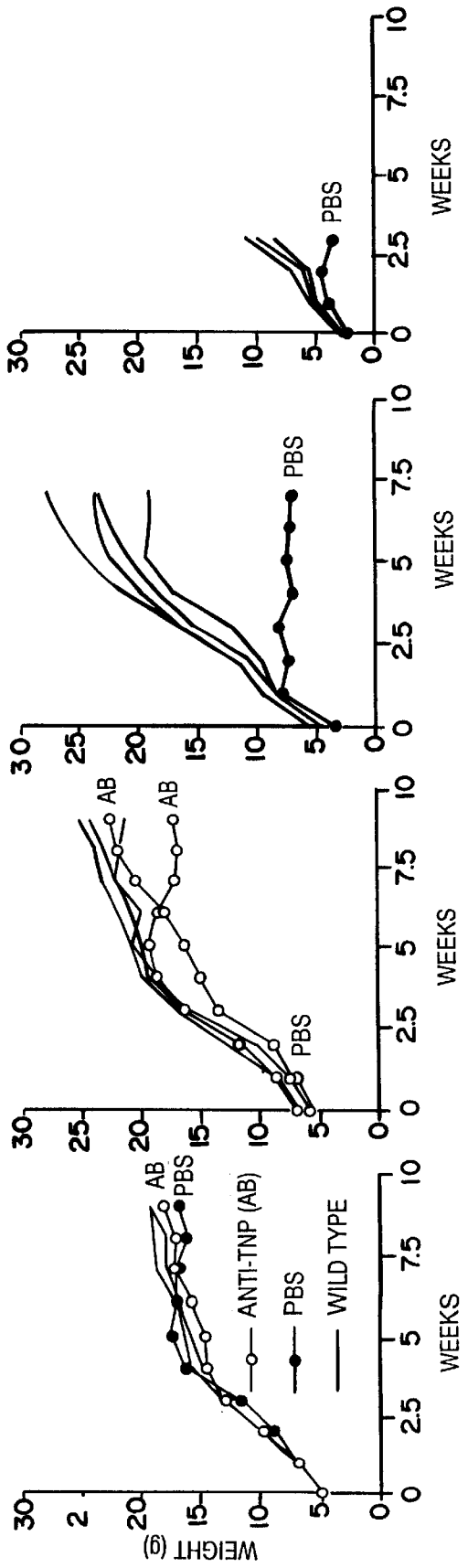

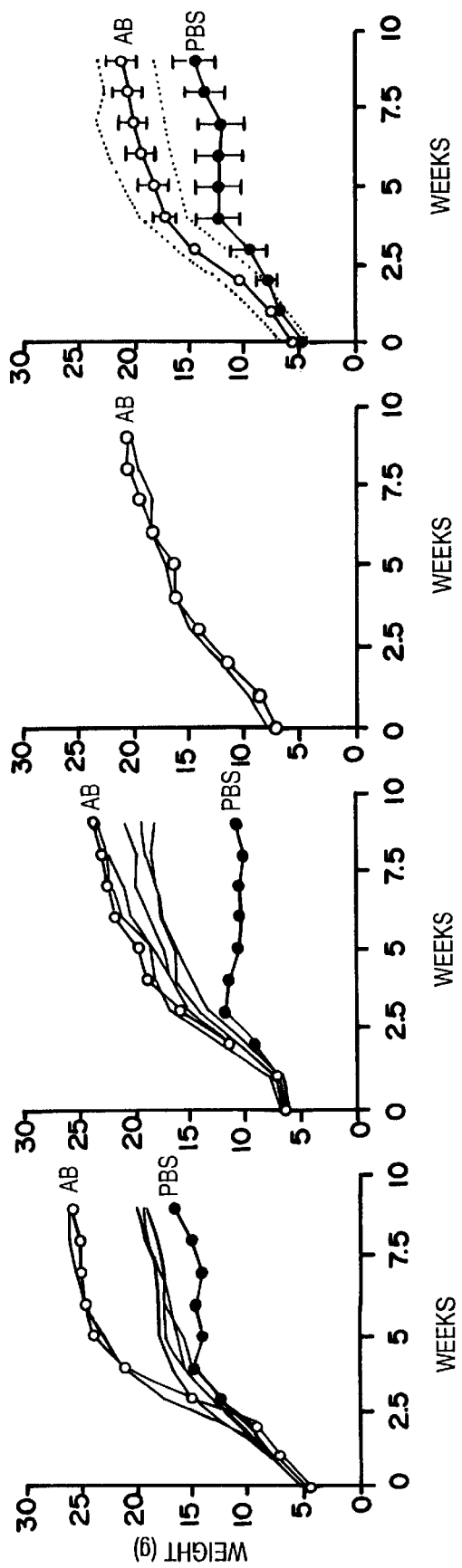

METHOD OF SCREENING A COMPOUND FOR ITS ABILITY TO ENHANCE THE ABILITY OF TRISTETRAPROLIN TO INHIBIT TUMOR NECROSIS FACTOR

This application is a continuation of Ser. No. 08/648,773 filed May 16, 1996, abandoned.

TECHNICAL FIELD

The present invention relates, in general, to tristetraprolin (TTP) and, in particular, to methods of modulating levels of tumor necrosis factor α (TNFα) using TTP or nucleic acid sequences encoding same. The invention further relates to methods of screening compounds for their ability to inhibit TNFα biosynthesis, processing or secretion.

BACKGROUND

Tumor necrosis factor alpha (TNFα) is a potent cytokine that is released from many cell types, particularly, macrophages and monocytes. TNFα also exists in a cell-membrane bound, higher molecular weight form on cells, and this form also appears to mediate a variety of biological effects. TNFα is thought to have few roles in normal development and physiology; however, it exerts harmful and destructive effects on many tissues in many disease states (Tracey et al, Ann. Rev. Med. 45:491 (1994)). Disease states in which TNFα has been shown to exert a major pathogenetic role include septic shock syndrome, cancer cachexia, rheumatoid arthritis, etc. Many investigators and pharmaceutical companies are actively investigating agents and potential drugs that can block TNFα effects, either by blocking its synthesis or interfering with its binding to its surface receptors.

One example of this approach is the use of monoclonal antibodies to TNFα. These have been used in animal models of human disease, and in human conditions such as rheumatoid arthritis (Arend et al, Arthritis and Rheumatism 38:151 (1995)). There is no question that these antibodies temporarily relieve some of the signs and symptoms of this disease in man. However, their potential widespread use is compromised by many factors, especially the fact that they seem to be only temporarily (ie, a few months) effective. Other drawbacks include expense, the need for parenteral administration, the likelihood that anti-idotype antibodies will develop, etc.

The present invention relates to a novel approach to the treatment of diseases the effects of which are mediated, at least in part, through TNFα. This approach involves the protein tristetraprolin (TTP) and nucleic acid sequences encoding same.

TTP (Lai et al, J. Biol. Chem. 265:16556 (1990)), also known as Nup475 (DuBois et al, J. Biol. Chem. 265:19185 (1990)) and TIS11 (Varnum et al, Oncogene 4:119 (1989); Varnum et al, Mol. Cell. Biol. 11:1754 (1991)), is a widely distributed 33.6 kDa phosphoprotein encoded by the immediate-early response gene, Zfp-36 (Taylor et al, Nucl. Acids Res. 19:3454 (1991)). This gene has been mapped to chromosome 7 in the mouse, and the equivalent human gene, ZFP36, has been mapped to chromosome 19q 13.1 (Taylor et al, Nucl. Acids Res. 19:3454 (1991)). TTP is the prototype of a group of proteins containing two or more highly conserved putative zinc fingers of the CCCH class (Varnum et al, Mol. Cell. Biol. 11:1754 (1991); Taylor et al, Nucleic Acids Res. 19:3454 (1991); Gomperts et al, Oncogene 5:1081 (1990); Ma et al, Oncogene 9:3329 (1994)). In addition, the protein has been shown to bind $Zn^{++}$ and has been localized to the cell nucleus in mouse fibroblasts (DuBois et al, J. Biol. Chem. 265:19185 (1990)), suggesting that it may be a transcription factor. Serum or other mitogen stimulation of quiescent fibroblasts causes rapid serine phosphorylation and nuclear to cytosolic translocation of TTP (Taylor et al, J. Biol. Chem. 270:13341 (1995); Taylor et al, Mol. Endocrinol. 10:140 (1996)), both of which are likely to modulate its function in cells.

In the adult mouse, TTP mRNA is highly expressed in lung, intestine, lymph node, spleen, and thymus, with lower expression in adipose tissue, kidney, and liver, and negligible expression in skeletal muscle and brain (Lai et al, J. Biol. Chem. 265:16556 (1990); DuBois et al, J. Biol. Chem. 265:19185 (1990)). In the thymus, TTP mRNA is highly expressed in both cortical and medullary thymocytes, while in the spleen, it is highly expressed in B and T lymphocytes within the white pulp, and is expressed at somewhat lower levels in the myeloid cells of the red pulp and endothelial cells of the high endothelial venules. In addition, TTP is constitutively expressed in several types of blood cells, particularly neutrophils, macrophages and B and T lymphocytes. The function of TTP in normal vertebrate physiology, however, was heretofore unknown.

OBJECTS AND SUMMARY OF THE INVENTION

It is a general object of the invention to provide a method of modulating cellular levels of TNFα.

It is a specific object of the invention to provide a method of treating diseases and disorders associated with TNFα excess.

It is a further object of the invention to provide a method of identifying an individual at increased risk to the effects of TNFα excess.

It is another object of the invention to provide a method of selecting compounds for there ability to inhibit TNFα production, processing or secretion.

It is a further object of the invention to provide a TTP-deficient non-human mammal.

These objects are met by the present invention.

In one embodiment, the present invention relates to a method of inhibiting TNFα production, processing or secretion in a mammal. The method comprises increasing the level of TTP, or a TNFα production, processing or secretion-inhibitory polypeptide fragment thereof, in the mammal so that the inhibition is effected.

In a further embodiment, the present invention relates to a method of treating an effect of excess TNFα in a mammal. The method comprises administering to the mammal TTP, or polypeptide fragment thereof that inhibits TNFα production, processing or secretion, or agent that enhances a TNFα production, processing or secretion-inhibitory effect of TTP, in an amount sufficient to effect the treatment.

In yet another embodiment, the present invention relates to a method of identifying a subject susceptible to a TNFα associated disease or disorder. The method comprises isolating a DNA-containing biological sample from the subject, locating the TTP gene present in the DNA and comparing the nucleic sequence of the TTP gene with a wild-type TTP encoding sequence and thereby determining whether the TTP gene includes a mutation that renders the subject susceptible to the disease or disorder.

In a further embodiment, the present invention relates to a method of identifying a subject susceptible to a TNFα associated disease or disorder. The method comprises i) isolating a biological sample from the subject, ii) contacting the sample with a TTP binding partner under conditions such that complexation between TTP and the binding partner can occur, and iii) detecting the presence or absence of the complexation, or comparing the extent of the complexation with a control sample comprising wild-type TTP.

In another embodiment, the present invention relates to a method of screening a compound for its ability to enhance the ability of TTP to inhibit TNFα production. The method comprises i) contacting the compound with a sample comprising an expression construct comprising a TNFα encoding sequence, in the presence of TTP or TNFα production-inhibitory polypeptide fragment thereof, under conditions such that the TNFα encoding sequence can be expressed, and ii) determining the level of expression of the TNFα encoding sequence and comparing that level to a level of expression obtained in the absence of the compound.

In yet a further embodiment, the present invention relates to a method of screening a compound for its ability to enhance a TNFα transcription-repressor effect of TTP. The method comprises i) contacting the compound with a sample comprising an expression construct comprising a TNFα promoter sequence operably linked to an encoding sequence, in the presence of TTP or TNFα production-inhibitory polypeptide fragment thereof, under conditions such that the encoding sequence can be expressed, and ii) comparing the level of expression of the encoding sequence obtained to a level of expression obtained in the absence of the compound.

In another embodiment, the present invention relates to a method of screening a compound for its ability to enhance a TNFα mRNA translation-inhibitory effect of TTP. The method comprises i) contacting the compound with a sample comprising TNFα mRNA, in the presence of TTP or a TNFα translation-inhibitory fragment thereof, under conditions such that translation of the TNFα mRNA can be effected, and ii) determining the level of translation of the TNFα mRNA and comparing that level of translation of the TNFα mRNA to a level of translation of TNFα mRNA obtained in the absence of the compound.

In yet a further embodiment, the present invention relates to a TTP-deficient non-human mammal.

In another embodiment, the present invention relates to a method of screening or testing a compound for its ability to treat a symptom of excess TNFα. The method comprises administering the compound to a TTP-deficient non-human mammal and monitoring the effect of the compound on the symptom.

Further objects and advantages of the invention will be clear from the description that follows.

BRIEF DESCRIPTION OF THE DRAWINGS

FIG. 4. Effect of TNFα antibody injections on body weights. As described in the text, TTP −/− mice from seven litters (each litter is labeled A–G) were injected at weekly intervals starting on day 10 of age with either anti-TNF monoclonal antibodies (AB; open circles) or PBS (closed circles). Body weights were measured at weekly intervals and are shown here. Littermates of the TTP +/+ and +/− genotypes are indicated by the lines without symbols. TTP −/− mice from litters B, C and D that were injected with PBS died before completion of the experiments, which consisted of nine weekly injections. The means +/− SEM of the six antibody-injected animals and the six PBS-injected animals are shown in H; the normal range (mean+/− S.D.) from all of the control littermates (n=25) is indicated by the dashed lines in H. The differences between the AB and PBS means were significant (p<0.001 using Student's t test) at each time point after four weeks.

DESCRIPTION OF THE INVENTION

Figure 1A:
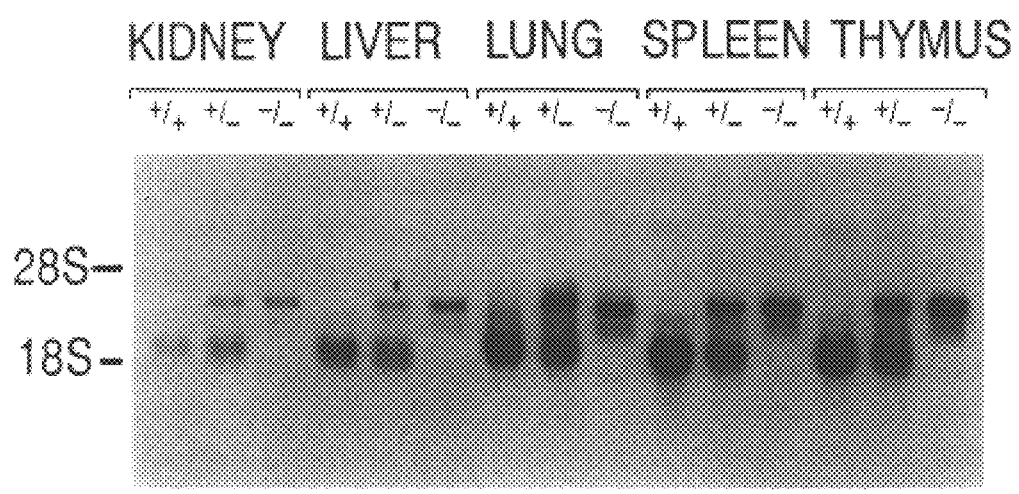
FIG. 1. Expression of TTP mRNA (a) and protein (B). (a) Total RNA was isolated from the indicated tissues of (+/+), (+/−), and (−/−) mice and subjected to northern blotting with a TTP cDNA probe. Each lane contains 15 μg of total cellular RNA. The lower band represents endogenous TTP mRNA, whereas the upper band represents the TTP-neo fusion RNA. (b) Primary embryonic fibroblasts were isolated from three different (+/−) (A–C) and three (−/−) (D–F) embryos. The cells were serum-deprived for 14 h, and then exposed to [$^{35}$S]-cysteine for 2 h and 20% fetal calf serum for an additional 2 h. Lysates from these cells were used for immunoprecipitation with an antibody that recognizes the amino-terminus of TTP, and the immunoprecipitated proteins were separated on a 9% acrylamide SDS gel and an autoradiograph prepared. The positions of molecular weight standards are indicated. TTP migrates at about 43 kDa. Immunoprecipitated proteins from the same samples were also separated on a 20% acrylamide SDS gel; no truncated amino-terminal TTP fragment was detected in the (−/−) samples.

The present invention results from the realization that TTP regulates effective levels of TNFα in animals, eg mammals. As indicated above, TNFα has been implicated in the pathology of a variety of neoplastic diseases, immune disorders and infections. Accordingly, the ability of TTP to regulate TNFα levels is of considerable pharmaceutical importance.

The identification of this regulatory activity of TTP makes possible methods of screening compounds for their ability to enhance the TNFα production-inhibitory activity of TTP, as well as their ability to enhance the effect of TTP on TNFα processing and secretion. It also makes possible methods of identifying susceptibility to TNFα-associated diseases, including inflammatory conditions and sepsis. Further, the demonstration of TTP as an inhibitor of TNFα production, processing or secretion makes possible new modes of therapy for diseases or disorders mediated by or exacerbated by TNFα.

It will be appreciated that the preferred subject of the invention is a human, however veterinary uses are also contemplated.

Compound Screens

The natural ability of TTP to inhibit cellular production, processing or secretion of TNFα permits the screening of test compounds for their ability to enhance this inhibitory effect. Using appropriate screens, compounds can be identified that potentiate the ability of TTP to inhibit TNFα production, processing or secretion, independent of the mechanism by which this inhibition occurs.

In one example of a screening system of the invention, a host cell is cotransfected with a vector encoding TTP and a vector containing the TNFα gene, for example, operably linked to a reporter gene. Examples of commonly used reporter genes include chloramphenicol acyltransferase (CAT), alkaline phosphatase, luciferase, growth hormone, thymidine kinase, etc. Potential host cells include fibroblasts, HeLa cells, and macrophage and lymphocyte cells lines. Transfection can be effected using art-recognized techniques.

Using this type of system, test compounds can be assayed for their ability to shift the TTP dose response curve to the left, that is, to decrease the dose at which TTP inhibits TNFα production (or processing or secretion) as measured, for example, by the reporter expression. Compounds identified as being capable of enhancing (directly or indirectly) the TTP inhibitory activity can then be further assayed, using standard protocols, for stability, toxicity etc.

While the foregoing screen can be used to assay test compounds for their ability to decrease the dose at which TTP inhibits TNFα production (or processing or secretion), various other screens can be devised based on the mechanism by which TTP exerts it inhibitory effect. For example, if TTP inhibits TNFα gene transcription, then a screen can be used in which sequences within the TNFα gene promoter are linked to a reporter gene. Such constructs can be used in cell transcription studies or cell-free transcription assays in the presence or absence of TTP and the test compound. Similarly, if TTP inhibits TNFα mRNA translation, test compounds can be added, for example, to cell-free translation assays in the presence or absence of TTP and TNFα mRNA. The rate of synthesis of the TNFα protein can then be determined. Other screens can also be used, dependent on the biochemical site of action of TTP (eg gene transcription, mRNA translation, protein processing or protein secretion).

Examples I–V below describe an animal model of TTP deficiency produced using gene targeting in murine embryonic stem cells. The resulting mice, while appearing normal at birth, develop a phenotype consistent with whole body TNFα excess. This animal model (as well as other such TTP-deficient animal (eg mammalian) models) can be used to screen and/or test agents for their ability to prevent/treat the effects of excess TNFα. The test agent can be administered to the model animal (eg orally or by injection) in accordance with standard test protocols and the effects on animal growth and phenotype monitored. Compounds that prevent the development of one or more aspects of the phenotype of TTP-deficient animals can then be further tested for pharmaceutical acceptability using standard protocols.

Detection/Diagnosis

The TTP deficiency produced in Examples I–V causes a severe syndrome of wasting and arthritis that is often lethal. Partial deficiencies resulting from the production of mutant forms of TTP, while perhaps non-lethal, can be expected to increase susceptibility to TNFα associated diseases and disorders, including infections, and autoimmune disorders (likewise, heterozygosity). The availability of the amino acid sequence of TTP (eg the human TTP sequence, Taylor et al, Nucl. Acids Res. 19:3454 (1991)) and its encoding sequence (eg GenBank accession number M63625) makes possible methods of identifying and diagnosing individuals at increased risk, for example, for inflammatory conditions or sepsis following infection.

General mutation screening of the TTP gene to identify subjects at increased risk can be performed by such methods as direct sequencing of cDNAs from candidate patients. Alternatively, approaches based on the cytogenetic mapping of the human gene to chromosome 19 q 13.1 (Taylor et al, Nucl. Acids Res. 19:3454 (1991)) can be used. For example, sequences from the human cDNA or genomic DNA can be used to locate the TTP gene (ZFP36) on a physical map of chromosome 19 (see, for example, Garcia et al, Genomics 27:52 (1995)). One or more polymorphic loci in the immediate vicinity of the gene can then be identified. Polymerase chain reaction (PCR) primers, for example, can be used to screen genomic DNA from populations (eg members of multiple families with rheumatoid arthritis) for polymorphisms closely linked to the TTP gene. Direct DNA sequencing of genomic DNA from likely candidate patients can then be accomplished using, for example, PCR sequencing strategies.

In an alternative approach, a biological sample can be obtained from a subject suspected of being at increased risk and the sample examined for the presence of a mutated form of TPP. Biological samples suitable for use in this regard include blood cells and transformed cell lines derived therefrom, lung lavage fluid, ascites fluid, etc. Tissue samples can also be used, including samples from liver, kidney intestine, spleen, lymph nodes, etc. Detection of a mutant form of the protein can be effected by isolating the protein from the sample and determining its amino acid sequence or by contacting the protein (in purified or semi-purified form) with a binding partner (eg an anti-wild type TTP antibody or TNFα promoter sequence) and determining whether complexation occurs. Complexation (or lack thereof) can be established using any of a variety of art recognized techniques (eg use of a labeled binding partner, use of a binding partner bound to a solid support, etc). Mutant forms of the protein can be expected to have altered (eg decreased) affinity for the binding partner. In addition, abnormalities in the size, charge or relative amount of the protein identified, for example, by means of a binding partner (such as an antibody) indicate a mutation in the TTP gene. Mutations can be confirmed by routine sequencing of the gene.

The identification of mutant forms TTP or its encoding sequence makes possible the identification of subjects likely to benefit from increased monitoring or therapeutic intervention.

Therapy

The present invention contemplates the use in gene therapy regimens of DNA sequences encoding TTP or portions thereof encoding TNFα production (processing or secretion)-inhibiting polypeptides. The encoding sequences can be present in a construct which, when introduced into target cells, results in expression of the TTP encoding sequences and thus production of the TNFα production (processing or secretion)-inhibitor.

For gene therapy to be practical, it is desirable to employ a DNA transfer method that: (1) directs the therapeutic sequence into specific target cell types (2) is highly efficient in mediating uptake of the therapeutic polynucleotide into the target cell population, and (3) is suited for use ex vivo or in vivo for therapeutic application.

Delivery of the TTP gene (or portion thereof encoding a TNFα production (processing or secretion)-inhibitor polypeptide) can be effected using any of a variety of methodologies. Presently available methodologies include transfection with a viral vector (eg retroviral vector or adenoviral vector) and fusion with a lipid. Other techniques are also available, many employing selectable markers to improve transfection efficiency. The technique selected depends upon the particular situation.

Retroviral vectors can be used to effect high efficiency gene transfer into replicating cells and such vectors are particularly suitable for use where target cells are present in a body compartment, such as brain and liver or epithelial surfaces such as lung, bladder or colon. Adenovirus vectors are advantageous from the standpoint that they have the potential to carry larger insert polynucleotide sequences than retroviral vectors and they have the ability to infect non-replicating cells. Further, they are suitable for infecting tissues in situ, especially in the lung. Adenoassociated viruses, which integrate, can also be used, as can other viral systems depending on the target site, including hepatitis virus when liver is the target tissue. Consistent with this approach, TTP sequences can be transfected into autologous bone marrow progenitor or stem cells, and those cells can then be transplanted back into the original donor, for example, after selection for cells expressing the transfected TTP sequences. Similar approaches are contemplated in the treatment of rheumatoid arthritis (Chernajorsky et al, Brit. Med. Bull. 51:503 (1995); Kiem et al, Curr. Opin. Oncol. 7:107 (1995)). (See also Morgan and Anderson, Annu. Rev. Biochem. 62:191 (1993) and Mulligan, Science 260:926 (1993) for further details relating to use of viral vectors for gene therapy.)

Another gene transfer method suitable for use in the present invention is the physical transfer of plasmid DNA in liposomes directly into target cells. Liposome-mediated DNA transfer has been described by various investigators (Liu et al, Gene Therapy 1:7 (1994); Huxley, Gene Therapy 1:7 (1994); Miller and Vile, FASEB J. 9:190 (1995)).

Essentially any suitable DNA delivery method can be used in the context of the present invention. Ex vivo transfection using viral vectors, however, may be preferred in certain settings. Use of the TTP gene truncated at the 3' untranslated region may serve to make the mRNA more stable. Alternatively, a TTP cDNA operably linked to a cell specific promoter can be used. In any case, transfection of hematopoietic marrow progenitors or stem cells ex vivo and reintroduction by bone marrow transplantation can be effected.

The nucleic acid-containing compositions of the invention can be stored and administered in a sterile physiologically acceptable carrier. The nucleic acid can be present in combination with any agent which aids in the introduction of the DNA into cells.

Various sterile solutions may be used for administration of the composition, including water, PBS, etc. The concentration of the DNA will be sufficient to provide a therapeutic dose.

Actual delivery of the gene sequence, formulated as described above, can be carried out by a variety of techniques including direct injection, administration to the lung and other epithelial surfaces, intravenous injection and other physical methods.

The present invention also contemplates the use of TTP, and TNFα production (processing or secretion)-inhibitor polypeptide fragments thereof, as a pharmaceutical agent to effect suppression of TNFα biosynthesis, processing or secretion. Polypeptides can be made using commonly used and widely available techniques for the synthesis of synthetic peptides. The TTP protein or polypeptide fragments thereof can be synthesized recombinantly using common expression systems such as $E.$ $coli$, baculovirus, Cos cells, etc. The protein/polypeptide can then be purified and used, for example, for injection or infusion as with many protein drugs currently available for clinical use. Alternatively, TTP can be isolated from natural sources, using art recognized techniques.

The TTP protein, or fragment thereof, can be administered by any appropriate means to achieve the effect sought (eg treatment of Type I diabetes, systemic lupus erythrematosis, rheumatoid arthritis or other inflammatory condition, tumor, infection, or the like). Parenteral administration is preferred, for example, periodic subcutaneous, intramuscular, intravenous, intraperitoneal or intranasal routes can be used using either bolus injection or gradual infusion. Alternatively, topical or oral administration can be used.

The optimum dosage administered will vary with the subject, the protein/polypeptide and the effect sought. Appropriate doses can be readily determined by one skilled in the art.

Compositions suitable for parenteral administration include sterile aqueous or non-aqueous solutions, suspensions or emulsions. Compositions can be present in other dosage unit form (eg tablet or capsule). Compositions suitable for topical administration can be in the form of a cream, gel, ointment, lotion or foam.

The compositions comprise the TTP protein/polypeptide, in an amount effective to achieve the desired result, together with a pharmaceutically acceptable carrier.

Certain aspects of the present invention are described in greater detail in the non-limiting Examples that follow.

EXAMPLES

The following experimental details pertain to the Examples I–V which follow.

Generation of TTP-deficient mice.

A TTP insertion targeting vector was created by first isolating a 3.8 kb Zfp-36 (TTP genomic) clone from a SV129 library (Stratagene, La Jolla, Calif.) using a mouse TTP cDNA probe (Lai et al, J. Biol. Chem. 265:16556 (1990)); this fragment was cloned into the SalI site of BS+ (Stratagene). A 1.14 kb XhoI-BamHI neo fragment from pMC1Po1A (Stratagene) was then ligated into the TTP SstI site (1 kb downstream of the initiator ATG) in pBS+/TTP. Next, a 4.9 kb SalI TTP-neo fragment from pBS+/TTP-neo was cloned into the SalI site of pSP73 (Promega, Madison, Wis.), into which two thymidine kinase genes (ClaI-BamHI and HindIII-XhoI fragments of pIC19R/MC1-TK) (Mansour et al, Nature 336:348 (1988)) had been cloned previously at the pSP73 ClaI-BamHI and HindIII-XhoI sites. This targeting vector was linearized with HindIII and electroporated into ES cells, which were then used to generate chimeric mice according to established methods (Koller et al, Proc. Natl. Acad. Sci. USA 86:8932 (1989)).

Northern blot analysis.

Dissected tissues were rapidly frozen in liquid nitrogen, pulverized in liquid nitrogen, and then homogenized in a guanidinium thiocyanate solution, as described previously (Stumpo et al, Proc. Natl. Acad. Sci. USA 86:4012 (1989)). Total cellular RNA was isolated from the tissue lysate using an established acidic phenol extraction procedure (Chomzynski and Sacchi, Anal. Bioch. 162:156 (1987)). 15

μg RNA samples were separated by electrophoresis in 1.2% agarose/formaldehyde gels and used for northern blotting (Stumpo et al, Proc. Natl. Acad. Sci. USA 86:4012 (1989)) with a [$^{32}$P]-labeled mouse cDNA probe (Lai et al, J. Biol. Chem. 265:16556 (1990)).

Cell culture and immunoprecipitation.

Primary embryonic fibroblasts were prepared (Robertson, Robertson, E. J., ed. (IRL Press, Oxford) pp. 77–78 (1987)) from 14–17 day mouse embryos that had been generated from TTP(±) mouse matings. To identify (+/−) and (−/−) cell lines, DNA was isolated from the cells (Koller et al, Proc. Natl. Acad. Sci. USA 86:8932 (1989)), digested with EcoRI and subjected to Southern blot analysis (Stumpo et al, Proc. Natl. Acad. Sci. USA 86:4012 (1989)) using as a probe a 2.4 kb BstEII-HindIII TTP gene fragment (Taylor et al, Nucl. Acids Res. 19:3454 (1991)). Using this strategy, the 7.5 kB EcoRI fragment that resulted from a targeted TTP allele was easily distinguishable from the 10 kb EcoRI fragment that resulted from a wild-type TTP allele.

Cell labeling and immunoprecipitation protocols have been described (Taylor et al, J. Biol. Chem. 270:13341 (1995). Briefly, confluent 60 mm plates of cells were serum-deprived for 24 h in DMEM supplemented with 1% (w/v) bovine serum albumin, and then exposed to [$^{35}$S]-cysteine for 2 h and 20% (v/v) fetal calf serum for an additional 2 h. Next, the cells were lysed by brief sonication in a buffer containing 1% (w/v) nonidet P-40, 5 mM EDTA, 0.15M NaCl, and 50 mM Tris, pH8.3; protein was precipitated with an immunopurified polyclonal antiserum that recognized the 24 amino-terminal amino acids of TTP (Taylor et al, J. Biol. Chem. 270:13341 (1995)). Precipitated proteins were separated on 9% or 20% polyacrylamide SDS gels, which were dried and used for autoradiography.

Myeloid progenitor cell assays.

Assays were performed on femoral bone marrow, peripheral blood and spleen from +/+ and −/− mice at 33 days of age (young mice) or 6.5 to 12 months of age (adult mice). These were performed as described (Cooper et al, Exp. Hematol. 22:186 (1994)). Marrow, spleen and blood cells were respectively plated at concentrations of $2.5 \times 10^4$, $2.5 \times 10^5$ and $1.0 \times 10^5$ cells/ml in 1.0% methylcellulose culture medium with 30% fetal bovine serum (Hyclone, Logan, Utah), 0.1 mM hemin, 1 U/ml recombinant (r) human (hu) erythropoietin (Epo, Amgen Corp., Thousand Oaks, Calif.), 5% vol/vol pokeweed mitogen mouse spleen cell conditioned medium (PWMSCM), and 50 ng/ml r murine (mu) steel factor (SLF; Immunex Corporation, Seattle, Wash.). Colonies were scored after 7 days incubation at 5% $CO_2$ and lowered (5%) $O_2$. Calculation of the absolute numbers of progenitors per organ was based on the nucleated cellularity and colony counts for CFU-GM, BFU-E and CFU-GEMM in each organ for each individually assessed mouse. Cultures were also set up in methylcellulose or 0.3% agar (10% fetal bovine serum) in the presence or absence of different concentrations of Epo, rmu granulocyte-macrophage colony stimulating factor, rhu granulocyte colony stimulating factor, rhu macrophage colony stimulating factor (Immunex Corp) or PWMSCM with or without rmu SLF or rhu Flt-3 ligand (Immunex Corp) to assess the sensitivity of cells to stimulation by single or multiple cytokines.

Histological analysis.

Mouse tissues were immersed in Bouin's fixative for 2 to 4 days, and then washed for several days in 70% (v/v) ethanol at room temperature. When required, tissues were decalcified following Bouin's fixation by immersing in 12.5% (w/v) sodium citrate and 25% (v/v) formic acid for 24 h, rinsing in running water for 24 h, and then washing for several days in 70% ethanol, all at room temperature. Fixed tissues were then embedded for paraffin sectioning; 5–7 μm sections were stained with hematoxylin and eosin by standard methods, then photographed with a Nikon Opiphot-2 photomicroscope and Kodak Ektar 100 film.

Renal pathology was evaluated at 5 months of age. One kidney was fixed, embedded in paraffin and sectioned as described above prior to staining with hematoxylin and eosin, Congo red and periodic acid Schiff (PAS) (Tse, Mishell and Shiigi, eds. (W. H. Freeman and Company, New York), pp. 201–205 (1980)). The other kidney was quick frozen in OCT embedding compound on dry ice, and frozen sections were prepared for immunofluorescent microscopy using fluorescein-conjugated goat anti-mouse IgG or IgM as described (Andrews et al, Vet. Pathol. 31:293 (1994)).

Glomerular disease was graded by a pathologist blinded as to the genotype of origin of the kidney sections. Scores were determined using a grading system that assigns 0–3+ scores for proliferation, necrosis, crescent formation, vasculitis, and inflammatory infiltrate. IgG and IgM deposition were graded 0–3+ on the fluorescent slides by the same pathologist.

Fluorescent activated cell sorter (FACS) analysis.

Peripheral blood cells were obtained by capillary tube bleeding from the eye orbit; bone marrow cells were obtained by flushing dissected femurs with 2 mL ice cold RPMI 1640 medium followed by gentle pipeting to disperse the cells; and splenocytes and thymocytes were obtained by macerating dissected tissues with the plunger of a disposable 1 ml syringe in ice-cold RPMI 1640 medium, and then isolating the cells by density centrifugation (Tse, Mishell and Shiigi, eds. (W. H. Freeman and Company, New York), pp. 201–205 (1980)). Some peripheral blood and bone marrow cells were stained with ACCUSTAIN Wright Stain (3WS10) as described by the manufacturer.

Analysis of cell surface phenotype was performed on the cell preparations according to previously described direct and indirect-immunofluorescence assays (Haynes et al, New Engl. J. Med. 304:1319–1323 (1981)), using a FACStar Plus Flow Cytometer and associated software (Becton Dickinson). The following directly conjugated monoclonal antibodies were used at saturating titers: Thyl.2 (anti-Thy-1, Becton Dickinson, Mountain View, Calif.), Ly-5 (anti-B220, Caltag, South San Francisco, Calif.) Lyt2 (anti-CD8, Becton Dickinson), L3T4 (anti-CD4, Becton Dickinson), OX-12 (anti-rat, Sera-Labs, Crawley Down, Sussex, England), and streptavidin-phycoerythrin (Pharmingen, San Diego, Calif.). PK-136 (American Type Culture Collection (ATCC) HB191) was purified from serum-free media (Gibco, Grand Island, N.Y.) hybridoma culture supernatant using affinity chromatography over a Staphylococcal protein (A/G) column (Pierce, Rockford, N.Y.), then fluorescein conjugated and used at saturating titer. The following hybridomas were cultured in serum-free medium and supernatant was used in indirect immunofluorescence flow cytometry assays using fluorescein-conjugated OX-12 as a secondary reagent: F4/80 (ATCC HB198), 14.8 (ATCC TIB164), Gr-1 (RB6-8CA, a gift of R. L. Coffman, DNAX, Palo Alto, Calif.), Ter119 (a gift of I. L. Weissman, Stanford University), and Y3-Ag1.2.3 (ATCC CRL 1631).

Evaluation of autoimmunity.

DNA from calf thymus was purchases from the Sigma Chemical Co. DNA was dissolved in SSC (0.15M Na citrate, pH8) prior to purification by phenol extraction. Double-stranded DNA (dsDNA) was obtained by treating the DNA with $S_1$ nuclease while single-stranded DNA (ssDNA) was obtained by boiling for 10 min prior to rapid immersion in ice.

Sera obtained as described above were tested for reactivity to DNA antigens by ELISA as previously described (Gilkeson et al, J. Immunol. 151:1343 (1993)). Briefly, 96 well polystyrene plates were coated with DNA diluted to 5 µg/ml in SSC. Antigens used in these assays were calf thymus dsDNA (dsDNA) and calf thymus single stranded DNA (ssDNA). After addition of DNA, plates were incubated for 2 h at 37° C. for ssDNA assays and 16 h at 37° C. for dsDNA assays. Two-fold serial dilutions of sera in PBS-T (phosphate buffered saline containing 0.05% Tween 20) were then added to the plates starting at a 1/100 dilution. Following incubation, peroxidase conjugated goat-anti-mouse IgG was added. 3,3' 5,5' Tetramethylbenzidine (TMB) in 0.1M citrate (pH4) with 0.015% $H_2O_2$ was added for color development. $OD_{380}$ absorbance was determined by a microtiter plate reader (Molecular Dynamics, Menlo Park, Calif.).

Rheumatoid factor (RF) activity in the sera was also determined by ELISA. For IgM RF assays, microtiter plates were coated with mouse IgG (Sigma) at 1 µg/ml in PBS; for IgG RF assays, plates were coated with 1 µg/ml of rabbit IgG in PBS. After blocking with 1% BSA in PBS, sera were added in dilutions beginning at a 1/100 dilution. Peroxidase conjugated goat anti-mouse IgG (γ chain specific) or goat anti-mouse IgM (µ chain specific) were added to the plates followed by the substrate. After color development, absorbance at $OD_{380}$ was determined.

*Crithidia luciliae* assays for anti-dsDNA were performed as suggested by the manufacturer (Kallestad, Austin, Tex.). Sera were tested at 1/20 and 1/50 dilutions.

Antinuclear antibody assays were performed as suggested by the manufacturer (Zeuss Scientific, Raritan, N.J.). Sera were tested at 1/20 and 1/50 dilutions.

TNFα antibody administration.

To test the possible role of TNFα in the development of the TTP-deficient phenotype, six −/− mice received weekly intraperitoneal injections of a hamster monoclonal antibody (TN3-19.12) that is specific for mouse TNFα (Sheehan et al, J. Immunol. 142:3884 (1989)); a general gift from Dr. Robert D. Schreiber, Washington University School of Medicine) and six −/− mice received an equivalent volume of PBS. The first injection occurred when the animals were 10 days of age, and continued at weekly intervals for a total of nine injections. The first two injections were 125 µg of antibody in 50 µl PBS, and the last seven injections were 250 µg of antibody in 100 µl of PBS. One week after the final injection, the animals were killed with $CO_2$, and blood and tissues were harvested for blood counts and histology as described above.

EXAMPLE I

Generation of TTP (−/−) Mice

A targeting vector was constructed that contained 3.8 kb of the gene encoding TTP, Zfp-36 (Taylor et al, Nucl. Acids Res. 19:3454 (1991)), in which a neomycin resistance gene (neo) was inserted into the protein-coding portion of the second exon. Insertion of this sequence introduced multiple stop codons upstream of the sequences encoding the two putative zinc fingers, precluding synthesis of functional TTP protein. Using this targeting vector and established experimental methods (Koller and Smithies, Proc. Natl. Acad. Sci. USA 86:8932 (1989)), TTP-deficient mice were generated. Among the first 492 offspring of heterozygous (+/−) crosses, 126 (26%) were homozygous wild-type (+/+), 267 (54%) were heterozygous (+/−), and 99 (20%) were homozygous null (−/−), indicating that there was no substantial embryonic lethality associated with the (−/−) genotype.

Figure 1B:
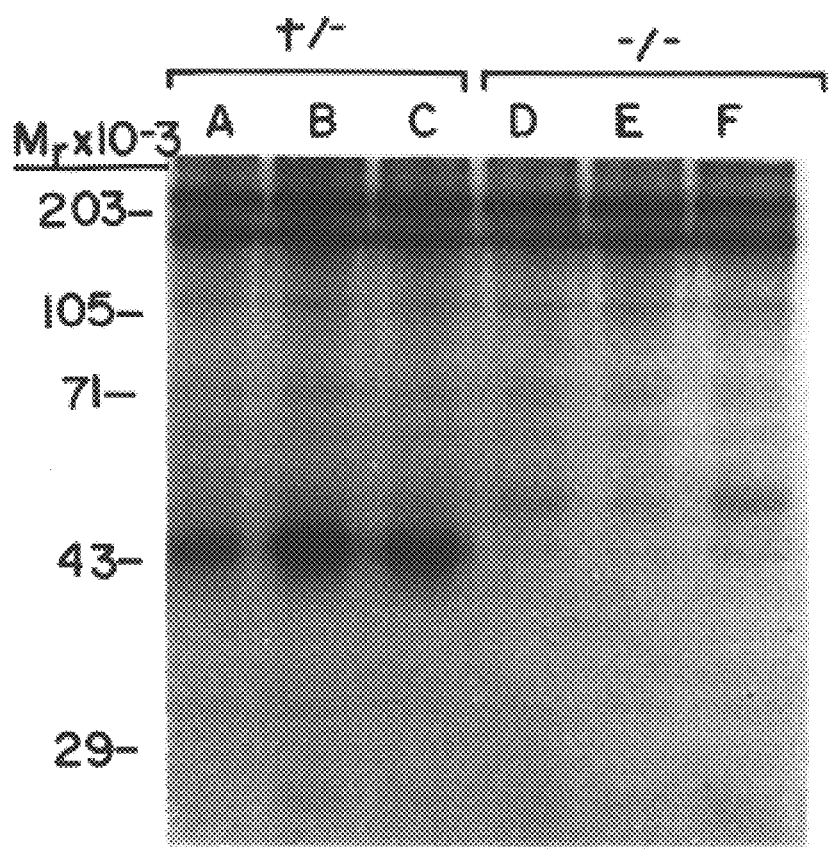

Northern analysis of tissues from (+/−) mice revealed that the endogenous TTP mRNA signal was decreased by about 50%, and that a TTP/neo fusion mRNA had been generated (FIG. 1a). No endogenous TTP mRNA was detected in tissues from a (−/−) mouse, but the TTP/neo fusion mRNA signal was increased over that seen in the +/− mice. Because the neo portion of the TTP/neo fusion mRNA contains many termination codons, a complete TTP/neo translation product should not be made; however, translation of an amino-terminal TTP fragment could have occurred. To test this possibility, primary embryonic fibroblasts were generated from both (+/−) and (−/−) embryos, and immunoprecipitations were performed on lysates from these cells, using an antibody (Taylor et al, J. Biol. Chem. 270:13341 (1995)) directed at the amino-terminus of TTP (FIG. 1b). Although TTP was readily detectable in (+/−) cells, neither intact TTP nor a truncated amino-terminal TTP fragment could be detected in the (−/−) cells (FIG. 1b).

The expression of two other mRNAs that encode related CCCH zinc finger proteins was also measured to determine if their expression was compensatorily increases in TTP-deficient mice; however, no change in expression of either TIS11B (cMG1) (Varnum et al, Oncogene 4:119 (1989), Taylor et al, Nucl. Acids Res. 19:3454 (1991)) or TIS11D (Varnum et al, Mol. Cell Biol. 11:1754 (1991)) was noted.

EXAMPLE II

Histological Characteristics of TTP (−/−) Mice

Figure 2:
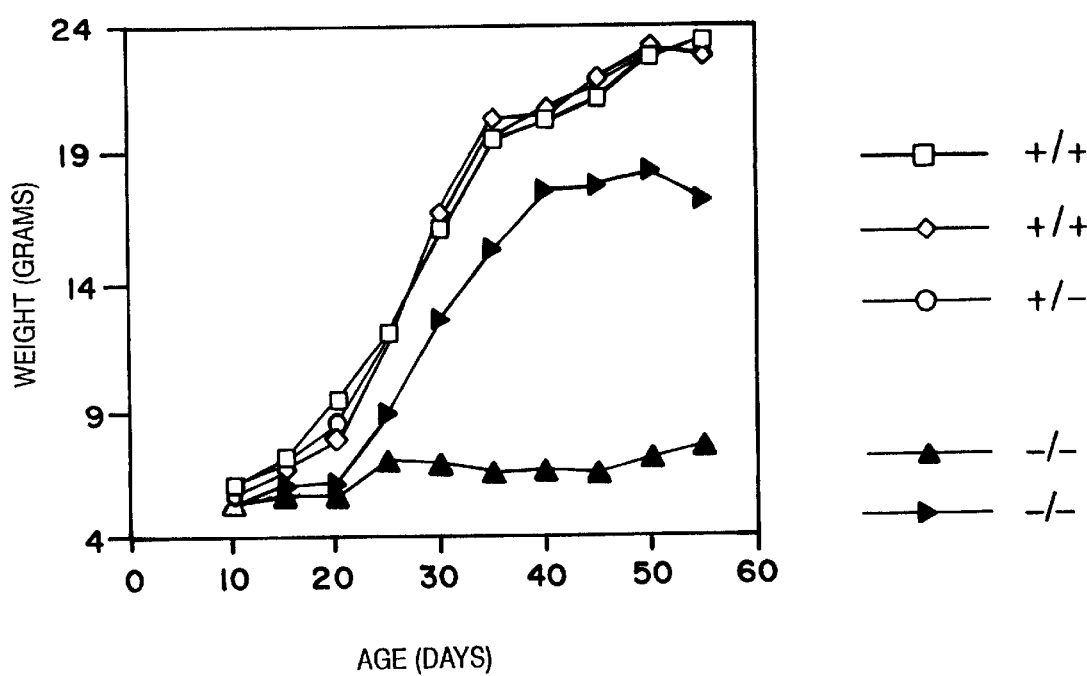
FIG. 2. Growth curves of two −/− and three +/+ or +/− littermates. Weekly weights of one litter of five pups were determined; genotypes of each mouse are indicated to the right.
Figure 3A:
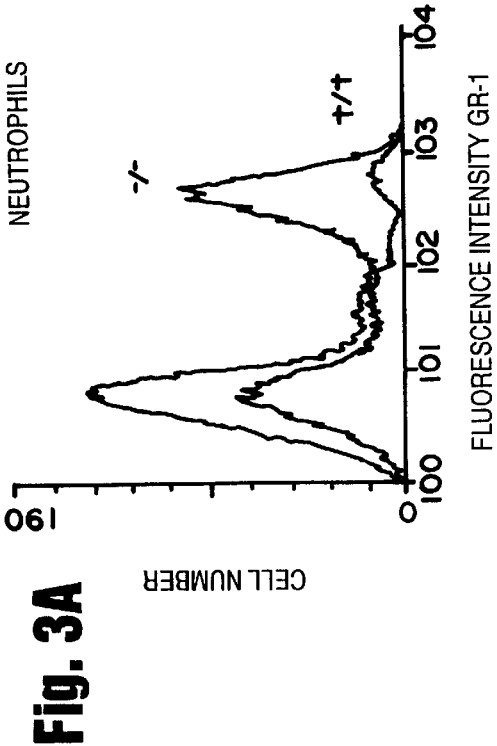
FIG. 3. Flow cytometric analysis of (a) Gr-1$^+$ neutrophilis, (b) Ly-5$^+$ lymphocytes, (c) Thy-1 T lymphocytes, and (d) F4/80$^+$ monocytes/macrophages, in peripheral blood adult (+/+) and (−/−) mice. Cell surface analysis was performed using a Becton Dickinson FACStar Plus flow cytometer and the accompanying software. Shown are the results from representative mice. The average percent positive cells and average absolute number of positive cells per mm$^3$ (± SEM) from 5–7 adult mice were: Gr-1: (+/+) 23±4%, 1.13±0.27×10$^3$; (−/−) 48±2%, 4.36±0.72×10$^3$; Ly-5: (+/+) 26±3%, 1.36±0.28×10$^3$; (−/−) 6±1%, 0.71±0.15×10$^3$; Thy-1: (+/+) 33±6%, 1.67±0.53×10$^3$; (−/−) 33±3%, 3.41±0.39×10$^3$; F4/80: (+/+) 5±1%, 0.29±0.05×10$^3$; (−/−) 8±2%, 0.87±0.26×10$^3$. Similar analyses from spleen and bone marrow are discussed in the text.
Figure 3B:
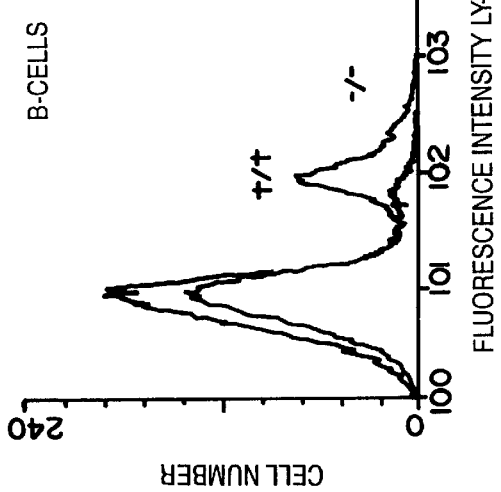
Figure 3C:
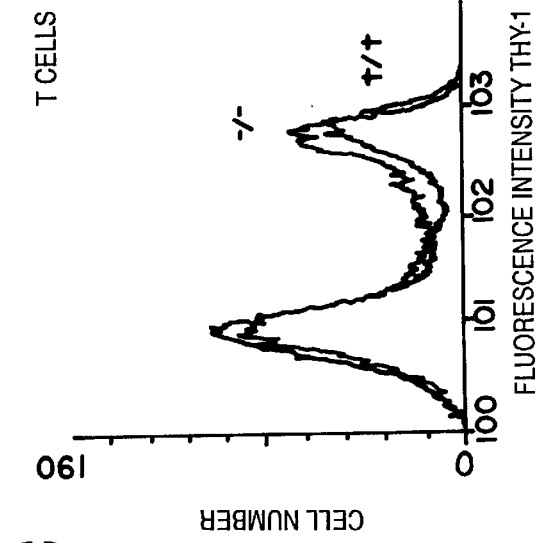
Figure 3D:
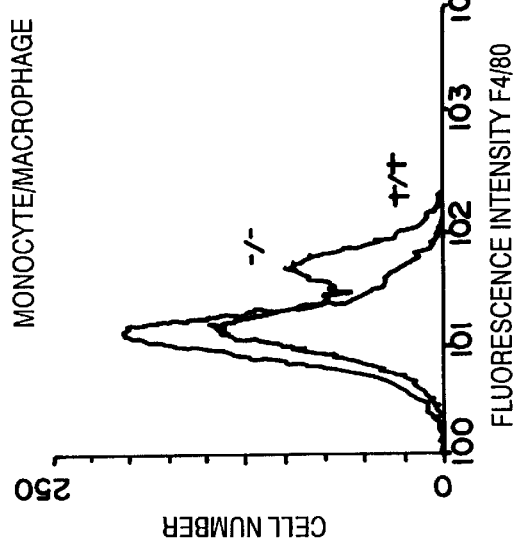

The (−/−) mice appeared normal at birth, but their rate of weight gain began to decrease compared to littermates between one and eight weeks after birth (FIG. 2). This failure of weight gain and eventual cachexia was one of the most striking characteristics of the phenotype, and occurred in essentially all of the mice to varying degrees (FIG. 2). They also developed patchy alopecia, dermatitis, arthritis, and conjunctivitis. Although all (−/−) mice eventually developed the syndrome, the degree to which they were affected was variable. 34% (of 56) were severely affected and died before reaching seven months of age. The remaining (−/−) mice were less severely affected, but nevertheless, 68% (of 37) displayed dermatitis, 88% arthritis, and 72% conjunctivitis by seven months of age. Survival of a (−/−) mouse was 16 months or more.

Histological examination of the (−/−) mice demonstrated several characteristic abnormalities. In the calavarial skin of seven-month old littermate mice, there was orthokeratotic hyperkeratosis in many areas, with an infiltration of neutrophils in the epidermis, and marked acanthosis. There was also diffuse inflammation in the underlying dermis, characterized by accumulation of many neutrophils and fewer lymphocytes, plasma cells, and macrophages. The inflammatory infiltrates extended to the deep dermal margins of the tissue, and in some cases, to the underlying skeletal muscle. Large numbers of Gr-1[+] neutrophils were present in both the epidermis and the dermis, while small foci of CD3[+], $TCR_{\alpha\beta}$[+], and Thy1.2[+] lymphocytes, 75% of which were of the CD4[+] subset, were also present in the dermis. A striking finding was that subcutaneous fat was essentially absent as was mesenteric and epididymal fat.

The epidermis of the eyelid was also thickened, was the palpebral conjunctiva. Neutrophils infiltrated the dermis beneath both the eyelid and the conjunctiva. In addition, there were relatively few mucous cells along the surface of the conjunctiva in the −/− mice.

In most joints in both the front and rear paws of the (−/−) mice at seven months of age, the synovium was markedly inflamed and thickened, with proliferating synovial cells extending well into the joint spaces; the synovium contained many Mac-1$^+$ macrophages and fewer Gr-1$^+$ neutrophils, CD3$^+$, TCR$_{\alpha\beta}^+$, and Thy1.2$^+$ lymphocytes and plasma cells. In addition, there was apparent proliferation of synovial cells and pannus formation, which in some cases completely separated apposing joint surfaces. Erosion of articular cartilage by pannus and extensive bone destruction were common. The marrow cavities were densely filled with cells of the myeloid lineage, especially mature neutrophils, and there was marked osteolysis of the inner aspect of the cortical bones.

Several abnormalities were also noted in the hematopoietic systems of the (−/−) mice. Thymuses in adult (−/−) mice were hypoplastic and showed no cortical/medullary organization; the thymuses of four days post-pactum (−/−) mice were decreased in size by an average of 50%. Spleens of the (−/−) mice were enlarged by an average of 41%, and there was extensive splenic myeloid hyperplasia, with many metamyelocyte, bands, and segmented neutrophils present. The perirenal, submaxillary, and mesenteric lymph nodes were also often enlarged, again showing extensive extramedullary hematopoiesis, primarily granulopoiesis. There was a marked increase in the number of myeloid cells in the bone marrow, which appeared nearly white in contrast to the red marrow of the control animals. Essentially all of the marrow myeloid cells were strongly Gr-1$^+$. Although the cellular architecture of the liver appeared normal in (−/−) mice, foci of necrotizing hepatitis were present that contained a mixed inflammatory exudate of neutrophils, macrophages, and lymphocytes. There was also an inflammatory abscess in the interventricular septum of one mouse.

Because antinuclear antibodies were present (see below), the kidneys were examined histologically by staining with hematoxylin and eosin, periodic acid Schiff (PAS), and Congo red, and immunologically, for the presence and absence of IgG and IgM. The tubular and interstitial architecture was essentially normal in the kidneys from the −/− mice, but the glomeruli manifested increased cellularity and increased PAS-positive mesangial matrix. There was also focal, segmental thickening of peripheral capillary loops, which were congested with erythrocytes. IgG and IgM staining of glomeruli were similar in the kidneys from the +/+ and −/− mice. Proteinuria was not increased in the −/− mice compared to control, nor were plasma BUN and creatine significantly elevated compared to control.

EXAMPLE III

Hematopoietic Cell Populations in TTP (−/−) Mice

To further characterize the hematopoietic abnormalities seen in the (−/−) mice, complete blood counts and flow cytometric analyses of leukocyte subsets were performed (FIG. 3). In the (−/−) mice, the total peripheral white blood cell count was elevated by more than two fold [10.5±1.3 (SEM)×10$^3$ (n=7) per mm$^3$ vs. 5.0±0.8×10$^3$ (n=6) per mm$^3$]. There was a marked increase in myeloid cells, with sharp increases in the number of Gr-1$^+$ neutrophils and F4/80$^+$ macrophages in peripheral blood and spleen, and in the number of Gr-1$^+$ neutrophils in bone marrow. The marrow myeloid cells were karyotypically normal, suggesting that they had not undergone malignant transformation. There were also increases in the number of PK136 natural killer cells in both peripheral blood and spleen. Conversely, there were smaller, less consistent decreases in B and T (B220) lymphocyte percentages and absolute numbers in hematopoietic tissues. Ly-5$^+$ B lymphocytes were decreased in peripheral blood, but were normal in spleen. The number of Thy-1$^+$ T lymphocytes in peripheral blood and spleen was normal, but the number of Thy-1$^+$ cells in bone marrow was decreased by two-fold. The peripheral red blood cell count, hemoglobin, hematocrit, and platelet count were within normal ranges; however, the Ter119$^+$ erythroid cells in bone marrow were decreased in percentage by about two-fold, presumably secondary to the massive increase of myeloid cells in the bone marrow.

Assays of hematopoietic progenitor cells per organ were performed on cells from spleen, bone marrow and peripheral blood of young (age 33 days) and older (6.5 to 12 months) mice. In the young mice, absolute numbers of granulocyte-macrophage progenitors (CFU-GM) from −/− mouse bone marrow were increased approximately two-fold compared to control (+/+ (n=3): 30.8+/−3.6×10$^3$/femur (mean±SEM); −/− (n=3): 64.3+/−0.5×10$^3$/femur, p<0.0025 using Student's t test) whereas CFU-GM from spleen and peripheral blood were unchanged. Erythroid (BFU-E) and multipotential (CFU-GEMM) progenitors per spleen, femur and ml of peripheral blood were not significantly different (p>0.05) in the young −/− and +/+ mice. In the older mice, there were marked increases in myeloid progenitors (CFU-GM, BFU-E and CFU-GEMM) in spleen and peripheral blood but not bone marrow from the −/− compared to +/+ mice. Comparative progenitor cell values ×10$^3$ per spleen (−/− vs. +/+) were 145±50 vs. 6±5 for CFU-GM, 115±51 vs. 7±4 for BFU-E and 10±4 vs. 0.2±2 for CFU-GEMM. Comparative values per ml of blood were 1530±781 vs. 46±39 for CFR-GM, 417±273 vs. 30±27 for BFU-E and 62±32 vs. 4±4 for CFU-GEMM. Colonies from young or old −/− or +/+ mice did not form in vitro without addition of growth factors and no obvious differences in sensitivity of progenitor cells to stimulation of proliferation by single or multiple cytokines was apparent with bone marrow cells from −/− vs. +/+ mice.

Routine serum chemistries, including glucose, were within normal limits in the (−/−) mice, except for slightly decreased albumin and increases total serum globulin and β-globulin levels.

EXAMPLE IV

Autoantibodies

Rheumatoid factors (both IgG and IgM) and anti-Sm antibody titers were repeatedly normal in sera from the −/− mice. However, ¾ of the sera from the −/− mice expressed high titers of antinuclear antibodies, with a homogenous pattern; these antibodies were not detected in ¼ sera from the +/+ animals. The −/− sera (but not the +/+ sera) also contained antibodies to double-stranded DNA (mean+/− SEM of ELISA units from four −/− mice was 0.41+/−0.18 compared to 0.06+/−0.02 from four +/+ mice; p=0.11 by Student's t test). This finding was confirmed by the Crithidia assay (¼ −/− mice were positive, compared to 0/4 +/+ mice). Finally, sera from the −/− mice (but not from the +/+ mice) contained high titers of antibodies to single stranded DNA (mean+/− SEM ELISA units from four −/− mice was 1.49+/−0.30 compared to 0.22+/−0.05 from four +/+mice; p=0.006 by Student's t test).

EXAMPLE V

TNFα Antibody Treatment

Because the phenotype of the TTP-deficient mice resembled that produced by chronic administration of TNFα

(Keffer et al, EMBO J. 10:4025 (1991); Ulich et al, Res. Immunol. 144:347 (1993)), an attempt was made to prevent the development of the phenotype by treating the mice beginning at 10 days of age with nine weekly intraperitoneal injections of a hamster monoclonal antibody (TN3-19.12) that is specific for mouse TNFα (Sheehan et al, J. Immunol. 142:3884 (1989)). This antibody was originally thought to cross-react with TNFβ (Sheehan et al, J. Immunol. 142:3884 (1989)); however, subsequent work has shown that it does not neutralize the biological activity of this cytokine (R. D. Schreiber, personal communication). Four of six TTP −/− mice injected with PBS exhibited striking growth retardation, and one exhibited mild growth retardation (FIG. 4A). The sixth PBS-injected mouse died before growth retardation could become obvious (FIG. 4B); two others died before completion of the trial (FIG. 4). Three PBS-injected mice survived the trial, but were strikingly smaller than their wild-type littermates (FIG. 4). In contrast, five of six mice injected with the TNFα antibody maintained essentially identical growth curves to those of their +/+ and +/− littermates (FIG. 4), whereas one exhibited slight growth retardation (FIG. 8B). The mean body weights of the six TTP −/− mice receiving the TNFα antibody were in the middle of the normal range throughout the trial, whereas the mean weights of those receiving PBS were significantly ($p<0.001$) lower than those receiving antibody at all time points after week 4 (FIG. 4H).

The antibody-injected mice also developed none of the cutaneous or joint stigmata associated with the −/− syndrome. In addition, the −/− mice injected with TNFα antibodies did not display medullary myeloid hyperplasia, with marrow from these animals containing 33.7±3.1% (SEM) mature granulocytes and bands, compared to 30.4±3.0% for the wild-type animals (p=0.49). Every examined aspect of the TTP-deficient phenotype has been essentially normalized by the injection of TNFα antibody.

All documents cited above are hereby incorporated in their entirety by reference.

One skilled in the art will appreciate from a reading of this disclosure that various changes in form and detail can be made without departing from the true scope of the invention.

What is claimed is:

1. A method of screening a compound for its ability to enhance the ability of tristetraprolin (TTP) to inhibit tumor necrosis factor (TNFα) production comprising
    i) contacting said compound with a sample comprising a TNFα encoding sequence, in the presence of TTP or TNFα production-inhibitory polypeptide fragment thereof, under conditions such that said TNFα encoding sequence can be expressed, and
    ii) determining the level of expression of said TNFα encoding sequence and comparing that level to a level of expression obtained in the absence of said compound.

2. A method of screening a compound for its ability to enhance a TNFα transcription-repressor effect of TTP comprising
    i) contacting said compound with a sample comprising a TNFα promoter sequence operably linked to an encoding sequence, in the presence of TTP or TNFα production-inhibitory polypeptide fragment thereof, under conditions such that said encoding sequence can be expressed, and
    ii) comparing the level of expression of said encoding sequence obtained to a level of expression obtained in the absence of said compound.

3. The method according to claim 2 wherein said encoding sequence encodes a reporter protein.

4. The method according to claim 2 wherein said encoding sequence encodes TNFα.

5. A method of screening a compound for its ability to enhance a TNFα mRNA translation-inhibitory effect of TTP comprising
    i) contacting said compound with a sample comprising TNFα mRNA, in the presence of TTP or a TNFα translation-inhibitory fragment thereof, under conditions such that translation of said TNFα mRNA can be effected, and
    ii) determining the level of translation of said TNFα mRNA and comparing that level of translation of said TNFα mRNA to a level of translation of TNFα mRNA obtained in the absence of said compound.

6. A method of screening a compound for its ability to enhance the ability of TTP to inhibit TNFα processing comprising
    i) contacting the compound with a sample comprising TNFα and TTP or TNFα processing-inhibitory polypeptide fragment thereof, and
    ii) determining the level of processed TNFα in said sample and comparing that level to a level obtained in the absence of said compound.

7. A method of screening a compound for its ability to enhance the ability of TTP to inhibit TNFα secretion from a cell comprising
    i) contacting a cell comprising TNFα and TTP or a TNFα secretion-inhibitory polypeptide fragment thereof, with said compound, and
    ii) determining the amount of TNFα secreted from said cell and comparing that amount to an amount obtained in the absence of said compound.

* * * * *